US007004972B2

(12) United States Patent
Yoon

(10) Patent No.: US 7,004,972 B2
(45) Date of Patent: Feb. 28, 2006

(54) TWO-INCISION MINIMALLY INVASIVE TOTAL HIP ARTHROPLASTY

(76) Inventor: Taek-Rim Yoon, 101-402 Bora Villa, #582 Unrim-dong, Dong-gu, Gwangju (KR)

( * ) Notice: Subject to any disclaimer, the term of this patent is extended or adjusted under 35 U.S.C. 154(b) by 0 days.

(21) Appl. No.: 10/700,008

(22) Filed: Nov. 3, 2003

(65) Prior Publication Data

US 2005/0096748 A1     May 5, 2005

(51) Int. Cl.
*A61F 2/32* (2006.01)
(52) U.S. Cl. ..................................... 623/22.4; 128/898
(58) Field of Classification Search .... 623/22.4–22.46, 623/23.15, 923, 22.21, 23.11; 606/86, 87, 606/89–91
See application file for complete search history.

(56) References Cited

U.S. PATENT DOCUMENTS

| 5,827,289 A * | 10/1998 | Reiley et al. ................... 606/86 |
| 6,443,988 B1 * | 9/2002 | Felt et al. ................. 623/17.12 |
| 6,676,706 B1 * | 1/2004 | Mears et al. ................ 623/22.4 |
| 6,723,102 B1 * | 4/2004 | Johnson et al. ................ 606/79 |
| 2003/0093152 A1 * | 5/2003 | Pedersen et al. ......... 623/14.12 |
| 2003/0220698 A1 * | 11/2003 | Mears et al. ................ 623/22.4 |
| 2004/0236341 A1 * | 11/2004 | Petersen ....................... 606/89 |
| 2005/0033293 A1 * | 2/2005 | Yoon ............................ 606/60 |

OTHER PUBLICATIONS

WK Chung, D Liu, LSS Foo, Mini-incision total hip replacement-surgical technique and early results, Journal of Orthopaedic Surgery 2004; 12(1): pp. 19-24.*
Chimento et al., "Minimally invasive total hip arthroplasty". *Operative Techniques in Orthopaedics*, vol. 11, No. 4, pp. 270-273 (2001).

Wenz et al. "Mini-incision total hip arthroplasty: a comparative assessment of perioperative outcomes". *Orthopedics*, vol. 25, No. 10, pp. 1031-1043 (2002).
Berger, "Mini-incisions: two for the price of one". *Orthopedics*, vol. 25, No. 5 (2002).
Waldman, "Minimally invasive total hip replacement and perioperative management: early experience". *Journal of the Southern Orthpaedic Association*, vol. 11, No. 4, pp. 213-217 (2002).
Berger, "The techniques and early results of the minimally invasive total hip arthroplasty". Symposia F presented at Advances in minimally invasive surgery of the Hip, New Orleans, LA (Feb. 5-9, 2003).
The Zimmer Institute Surgical Technique. "Minimally invasive total hip arthroplasty: the 2-incision procedure with VerSys beaded fullcoat plus and trilogy acctabular system". The Zimmer Institute (2003).

* cited by examiner

*Primary Examiner*—Alvin J. Stewart
(74) *Attorney, Agent, or Firm*—Hamre, Schumann, Mueller & Larson, P.C.

(57) ABSTRACT

A surgical procedure for replacing a destructed hip joint with an artificial joint is disclosed. The present invention provides a two-incision minimally invasive surgery for total hip arthroplasty. This method comprises positioning of the patient on a lateral decubitus position and a series of surgical techniques including a first skin incision over the anterior side of the trochanteric area of the femur (ranging from 3 cm to 10 cm), intermuscular dissection between the Gluteus muscle (Gluteus minimus and medius) and Tensor fascia lata muscle, incision of the anterior joint capsule, osteotomy of the femoral neck, removal of the femoral head and neck, acetabular reaming and socket insertion, secondary skin incision over the Gluteus maximus muscle (ranging from 1 cm to 6 cm), dissection through the muscle fiber of the Gluteus maximus, intermuscular dissection between the Gluteus medius and Piriformis, partial incision of the joint capsule, femoral reaming, femoral stem insertion, femoral head insertion, joint capsule closure and skin closure.

1 Claim, 6 Drawing Sheets

TWO-INCISION MINIMALLY INVASIVE TOTAL HIP ARTHROPLASTY

FIELD OF THE INVENTION

The present invention provides a surgical method for replacing a destructed hip joint with an artificial joint. The present invention is a two-incision minimally invasive surgery for total hip arthroplasty. This method comprises positioning of the patient in a lateral decubitus position and a series of surgical techniques including primary skin incision over the anterior side of the trochanteric area of the femur (ranging from 3 cm to 10 cm), intermuscular dissection between the Gluteus muscle (Gluteus minimus and medius) and Tensor fascia lata muscle, incision of the anterior joint capsule, osteotomy of the femoral neck, removal of the femoral head and neck, acetabular reaming and socket insertion, secondary skin incision over the Gluteus maximus muscle (ranging from 1 cm to 6 cm), dissection through the muscle fiber of the Gluteus maximus, intermuscular dissection between the Gluteus medius and Piriformis, incision of the joint capsule, femoral reaming, femoral stem insertion, femoral head insertion, joint capsule closure and skin closure.

The present invention provides a two-incision minimally invasive surgery which makes two small incisions rather than making one incision to perform total hip arthoplasty in order to minimize injury to the important muscles and joint capsule surrounding the hip joint. This invention is different from the previous two-incision method in that the operation is performed with the patient in a lateral decubitus position instead of a supine position, and the anterior incision approaches between the Gluteus muscle (Gluteus medius and minimus) and Tensor fascia lata muscle, rather than between the Sartorius and Tensor fascia lata. Therefore, this invention provides an easier and safer surgical technique in performing two-incision minimally invasive total hip arthroplasty.

BACKGROUND OF THE INVENTION

Total hip arthroplasty [FIG. 6] has been used since the 1960s for the treatment of destructed hip joints. Many surgical approaches have been used such as the anterior Smith-Peterson Approach, Watson-Jones Approach, Hardinge Approach, Direct lateral approach, Posterolateral approach (Modified Gibson approach), and Posterior Approach (Muller Approach). Each approach has advantages and disadvantages. For example, in the anterolateral approach, the Gluteus medius and Gluteus minimus are vulnerable to injury during the procedure or sometimes the muscle fibers are cut for easy insertion of the acetabular socket and then are repaired after the procedure. However, no matter how well or tightly they are repaired, muscle power is decreased, the time for rehabilitation is delayed, and sometimes patients complain of limping because of the weakness of the muscles. In the posterior or posterolateral approach, the short external rotator muscles (Piriformis, Gemellus superior and inferior, Obturator internus and externus, Quatratus femoris) are cut during the operative procedure. They may be repaired after the procedure but still remain very weak. Therefore, the postoperative rehabilitation is delayed and sometimes the artificial joint is dislocated because of the weakness of the muscles.

Many efforts have been made to give the patients less trauma during the operation and to permit early rehabilitation by performing a small incision.

There are several kinds of minimally invasive surgeries for total hip arthroplasty such as a one-incision anterior approach, one incision anterolateral approach, one-incision posterolateral approach, and two-incision approach. The two-incision approach (anterior and posterior incision) was made to be minimally invasive, minimizing injury not only to the skin but also to the muscles, ligaments, and joint capsules.

The present invention is a two-incision procedure. The anterior incision (3) is for acetabular socket insertion, and the posterior incision (4) is for the femoral stem insertion.

The previous method of the two-incision procedure was performed with the patient in a supine position [FIG. 1], causing femoral stem reaming to be much more difficult. Injury to the sciatic nerve was more likely to develop because the femoral insertion site was near the sciatic nerve, and finding the muscle plane between the Gluteus medius and Piriformis muscle in the supine position was more difficult. Also, in the previous technique, the anterior incision (1) approaches between the Sartorius muscle (7) and Tensor fascia lata muscle (8) and between the Rectus femoris muscle (18) and Tensor fascia lata muscle (8) distally which is more likely to injure the lateral femoral cutaneous nerve (11) because the incision is near the distribution of the lateral cutaneous nerve (11).

The present invention of the two-incision minimally invasive technique is different from the previous method in that the operation is performed with the patient in the lateral decubitus position [FIG. 2] which provides a much easier and safer position for the femoral stem insertion, and the anterior incision (3) approaches through a safer area between the Gluteus muscle (Gluteus medius and minimus) (9) and Tensor fascia lata muscle (8), rather than between the Sartorius muscle (7) and Tensor fascia lata muscle (8).

SUMMARY OF THE INVENTION

The present invention provides a surgical method for replacing a destructed hip joint with an artificial joint. This surgical procedure is performed with the patient in a lateral decubitus position. This method comprises surgical techniques including a first skin incision over the anterior side of the trochanteric area of the femur (ranging from 3 cm to 10 cm), intermuscular dissection between the Gluteus muscle (Gluteus minimus and medius) and Tensor fascia lata muscle, incision of the anterior joint capsule, osteotomy of the femoral neck, removal of the femoral head and neck, acetabular reaming and socket insertion, secondary skin incision over the Gluteus maximus muscle (ranging from 1 cm to 6 cm), dissection through the muscle fiber of the Gluteus maximus, intermuscular dissection between the Gluteus medius and Piriformis, incision of the joint capsule, femoral reaming, femoral stem insertion, femoral head insertion through anterior opening, joint capsule closure and skin closure. The characteristic of these procedures is to make two small incisions rather than making one big incision to perform total hip arthoplasty. The advantages of these procedures are that it causes less injury to the important muscles surrounding the hip joint and more preservation of the joint capsule. The purpose of these procedures is to minimize injury to the patient and to permit earlier rehabilitation for the patients with minimal pain.

BRIEF DESCRIPTION OF THE DRAWINGS

For a fuller understanding of the nature and objects of the invention, reference should be made to the following detailed description taken in conjunction with the accompanying drawings in which.

DETAILED DESCRIPTION OF THE INVENTION

Figure 1:
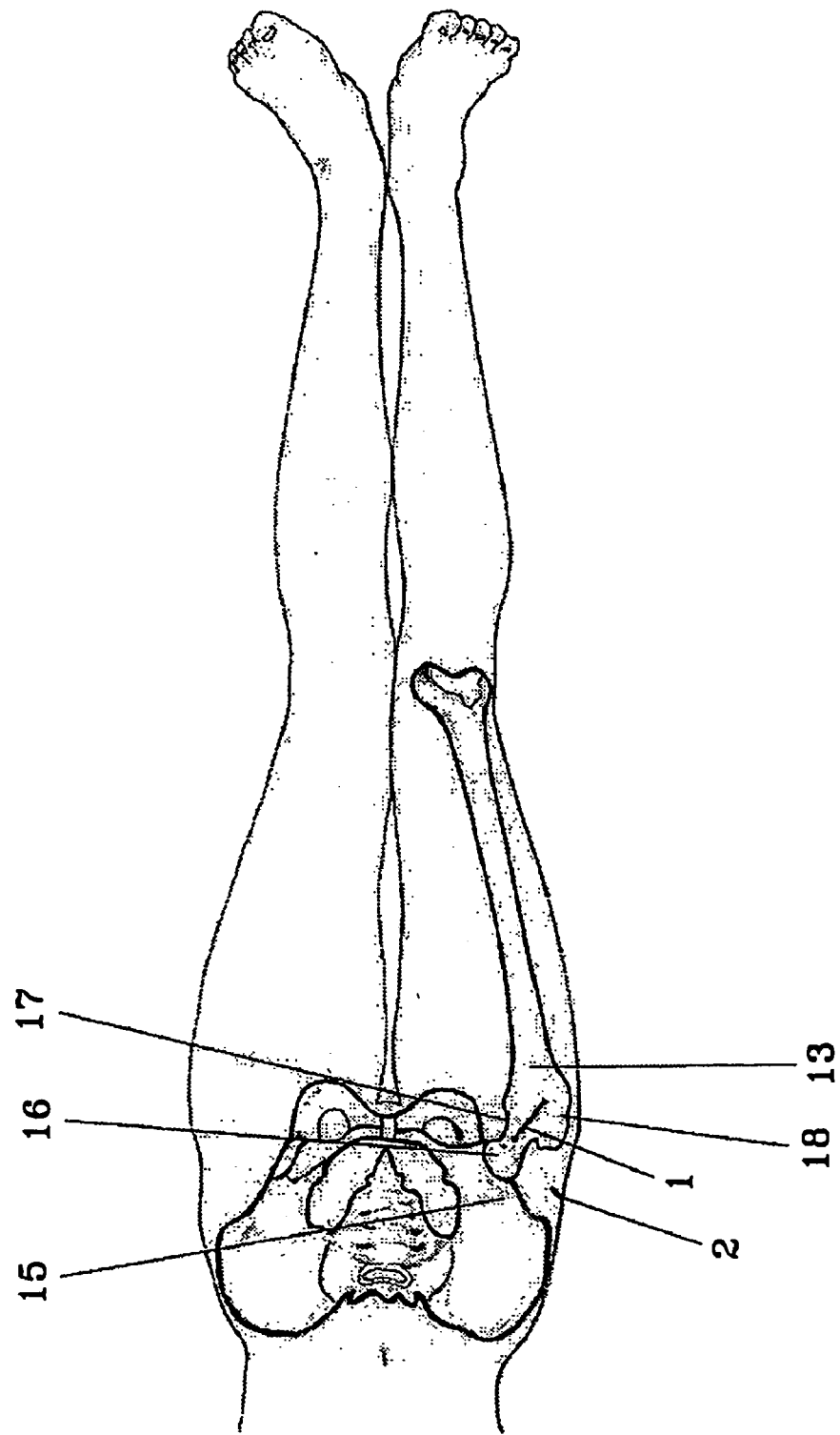
FIG. 1 is a schematic diagram for illustrating the supine position of the patient and the lines of skin incision (anterior (1) and posterior incision (2)) in the previous two-incision method.
Figure 2:
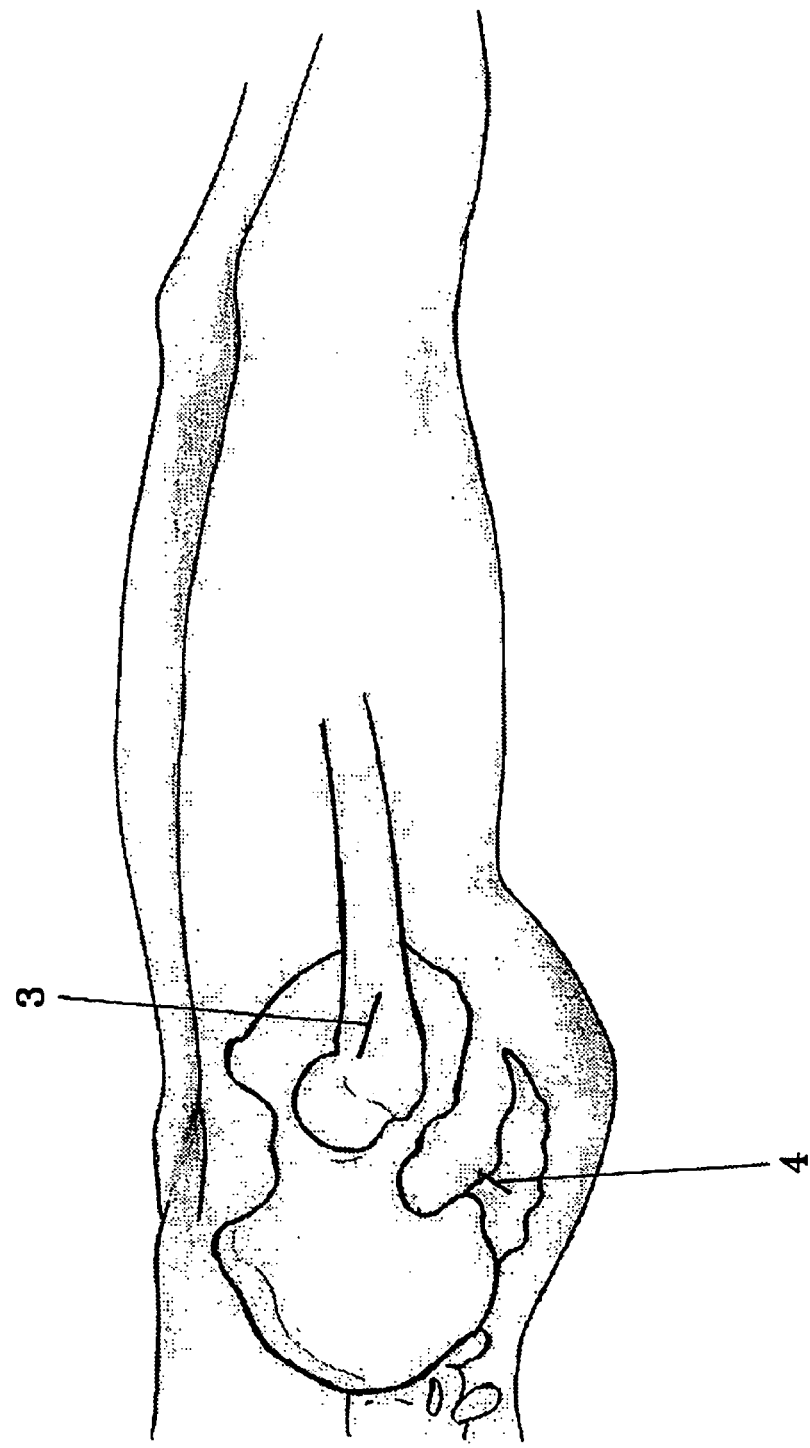
FIG. 2 is a schematic diagram for illustrating the lateral position of the patient and the lines of skin incision (anterior (3) and posterior incision (4)) in the present invention of the two-incision method.
Figure 3:
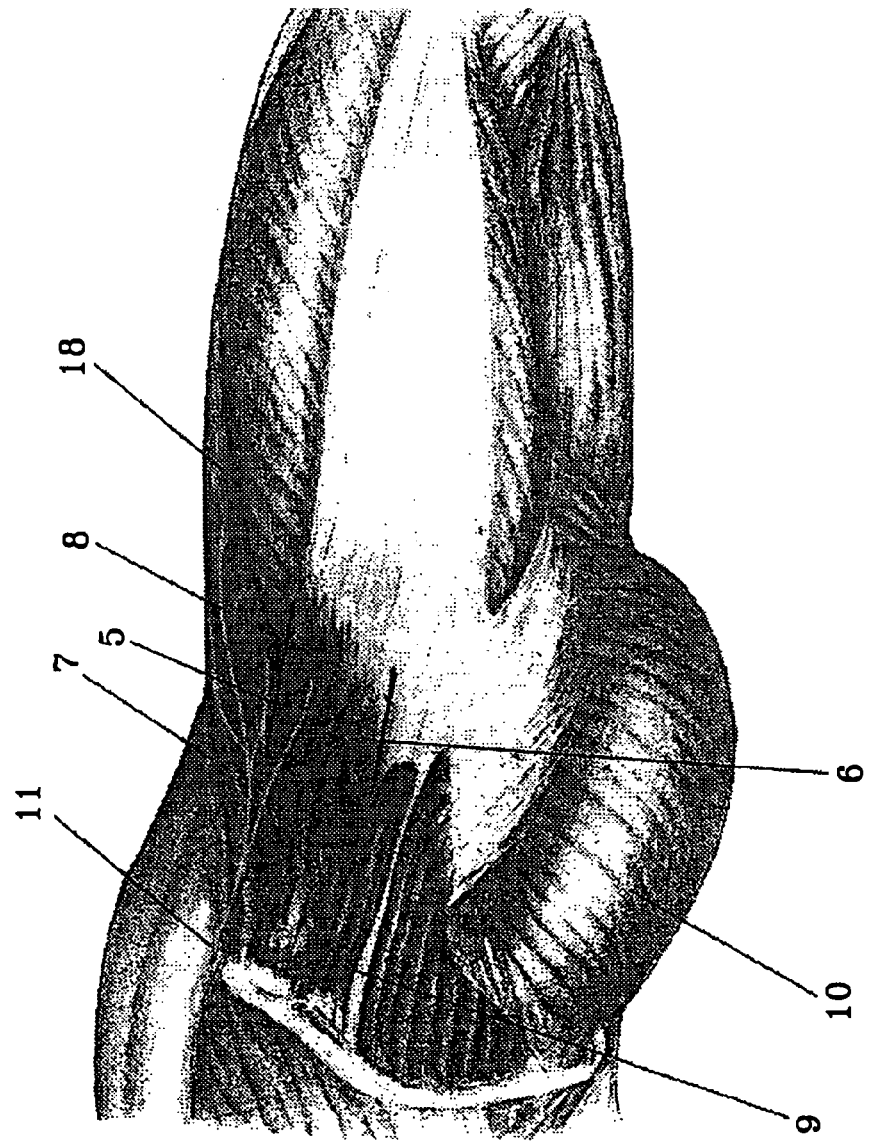
FIG. 3 is a schematic diagram for illustrating the relationship of the anatomic structures in the anterior incision showing the difference between the previous method (5) and the new method (6).
Figure 4:
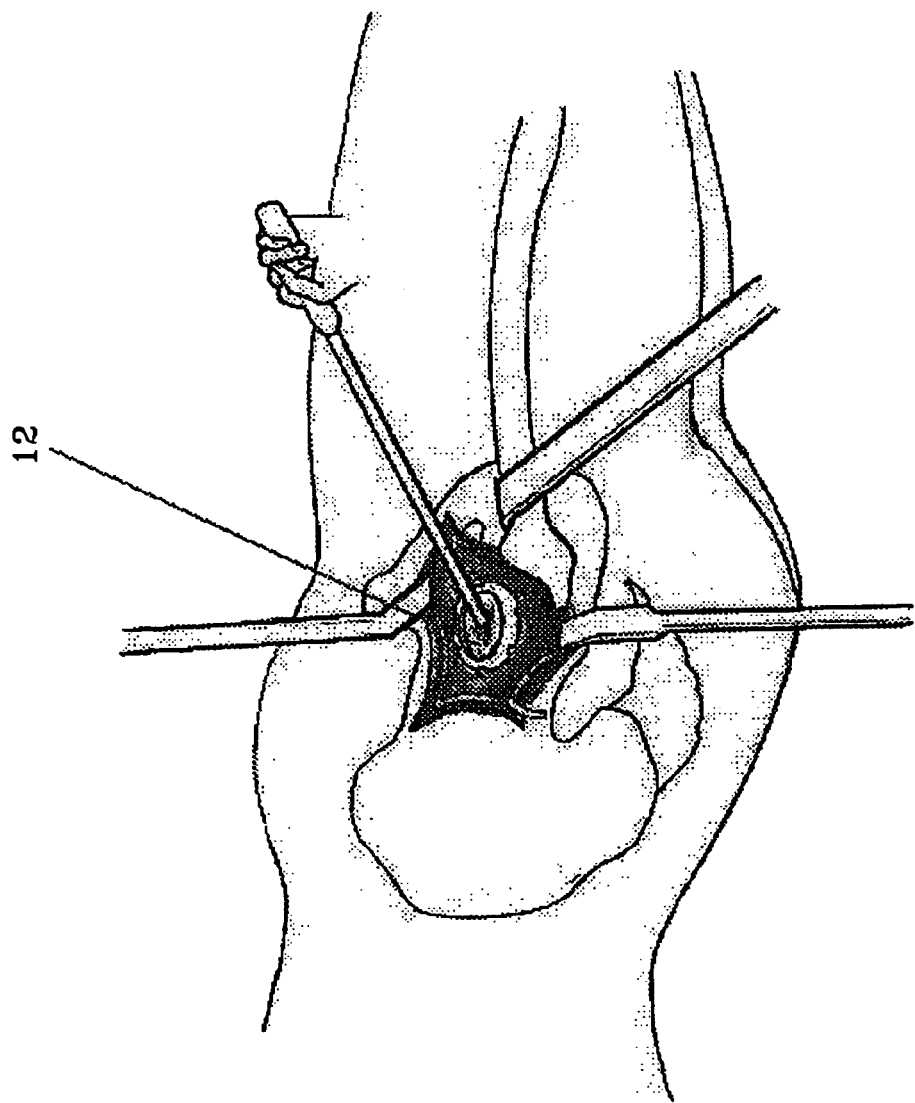
FIG. 4 is a schematic diagram for illustrating the insertion of the acetabular socket through the anterior skin incision (3, 6) in the lateral decubitus position.

A preferred embodiment of the present invention will now be described in detail with reference to the accompanying drawings. First, with the patient in a lateral decubitus position [FIG. 2] a skin incision (3) is made over the anterior side of the trochanteric area of the femur (ranging from 3 cm to 10 cm) (18). An intermuscular dissection (4) is made between the Gluteus muscle (Gluteus minimus and medius) (9) and Tensor fascia lata muscle (8). The anterior joint capsule is incised and the femoral neck (17) is exposed and osteotomized. The femoral head (16) and neck (17) are removed with a cork screw. The acetabulum (15) is reamed with a socket reamer and an acetabular socket (12) is inserted [FIG. 4].

Figure 5:
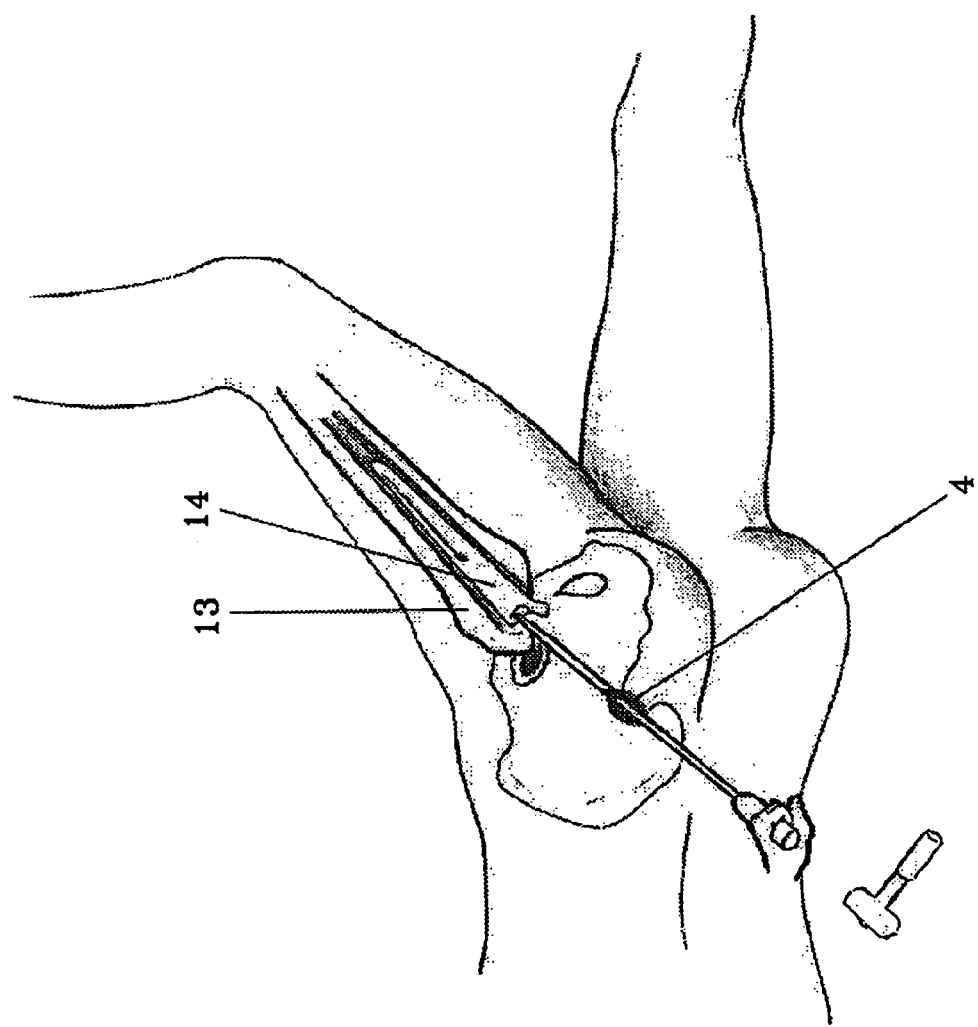
FIG. 5 is a schematic diagram for illustrating the insertion of the femoral stem through the posterior skin incision (4) in the lateral decubitus position.

A secondary skin incision (4) is made over the Gluteus maximus muscle (ranging 1 cm to 6 cm) (10). The muscle fibers of the Gluteus maximus (10) are spread and an intermuscular dissection between Gluteus medius and Piriformis is performed. The joint capsule is incised on the posterosuperior side of the hip joint. A tapered awl is introduced into the femoral canal. The proximal femur (13) is reamed with progressive larger reamers. The femoral stem (14) is inserted. The artificial femoral head is inserted through an anterior opening. The joint capsule, muscle fascia and subcutaneous tissue are repaired and the skin is closed [FIG. 5].

Figure 6:
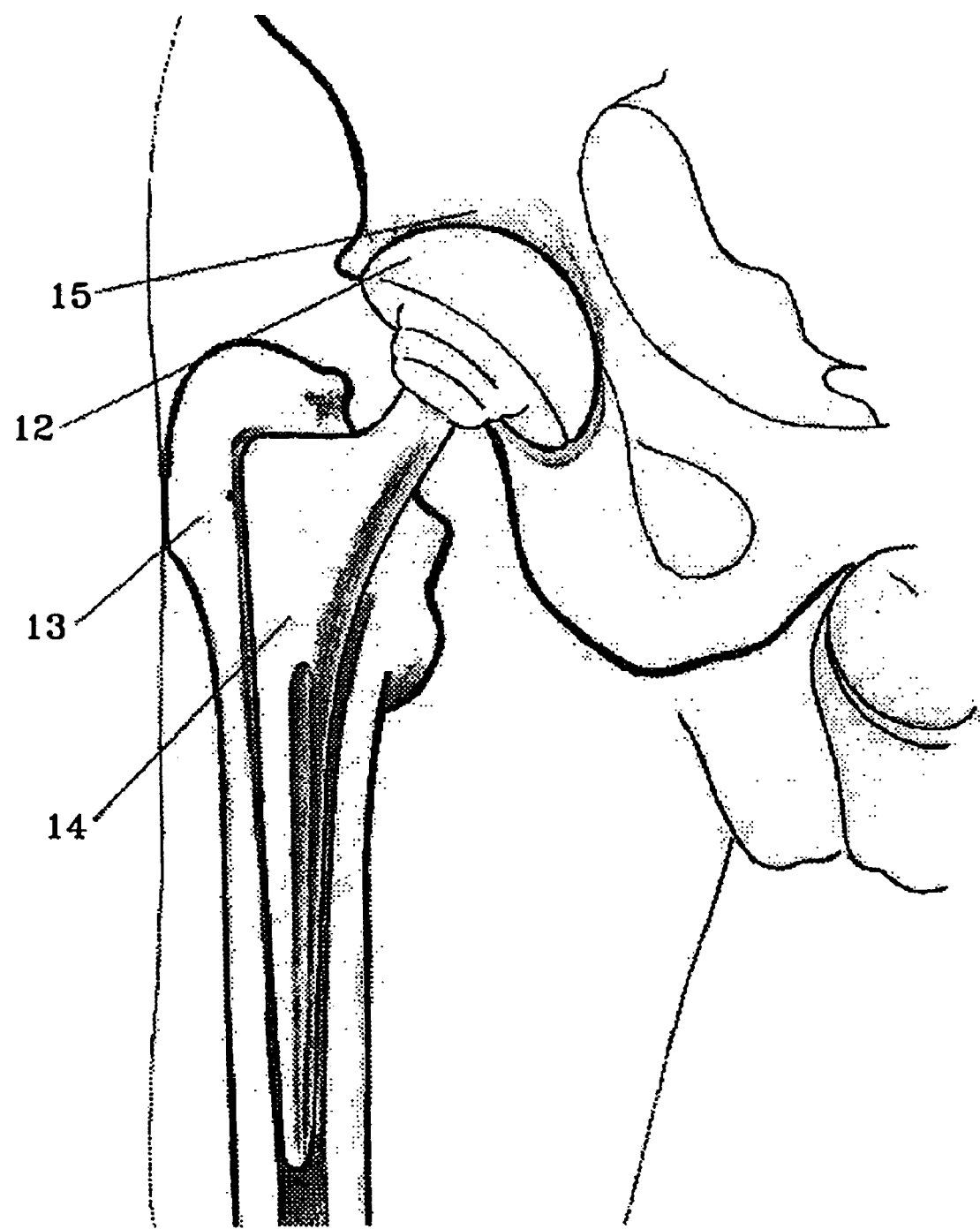
FIG. 6 is a schematic diagram for illustrating the final shape of the hip joint after total hip arthroplasty.

The characteristic of these procedures is to make two small incisions (3,4) rather than making one big incision to perform total hip arthroplasty [FIG. 6]. The advantages of these procedures are that it causes less injury to the important muscles surrounding the hip joint and more preservation of the joint capsule. The purpose of these procedures is to minimize injury to the patient and to permit earlier rehabilitation for the patients with minimal pain.

When the hip joint is severely damaged, arthroplasty must be performed to relieve pain and improve the function of the hip joint. During arthroplasty, surgical procedures such as skin incision, muscle cutting and capsule excision are necessary for the preperation and insertion of the components of artifical joints.

The present invention is a surgical method for replacing an destructed hip joint with an artificial joint by a minimally invasive method. The characteristic of these procedures is to make two small incisions: one anteriorly between the Gluteus muscle and Tensor fascia lata muscle (6) and another posteriorly through the muscle fibers of the Gluteus maximus and between the Gluteus medius and Piriformis muscle (4). The present invention is different from the previous method in that the operation is performed with the patient in a lateral decubitus position and the anterior approach goes between the Gluteus muscle (Gluteus medius and minimus) and tensor fascia lata muscle.

Femoral stem reaming is much more difficult if the previous two-incision approach is performed due to the supine position of the patient. Also, sciatic nerve palsy is more likely to develop for the previous two-incision approach because the femoral insertion site is near the sciatic nerve and the muscle plane between Gluteus medius and Piriformis muscle is hard to find. In the previous technique, the anterior approach goes between the Sartorius muscle and Tensor fascia lata which is more likely to injure the lateral femoral cutaneous nerve.

The present invention is different from the previous method in that the operation is performed with the patient in a lateral decubitus position which is much easier for C-arm fluoroscopic control for femoral reaming. In this position, the muscle plane between the Gluteus medius and Piriformis muscle is easily found and therefore the femoral stem reaming and insertion is much easier and safer than the supine position. Moreover, in this new method, the anterior incision approaches into a intermuscular plane between the Gluteus muscle (Gluteus medius and minimus) and tensor fascia lata muscle which minimizes injury of the lateral femoral cutaneous nerve, and with this approach the acetabular reaming can be performed without C-arm fluoroscopic control.

The present invention is intended to be minimally invasive and minimize injury not only to the skin, but also the muscles, ligaments, and joint capsules. The advantages of the present invention are that it causes less injury to the important muscles surrounding the hip joint and joint capsule, less chance of injury to the surrounding nerve, easy surgical technique, less bleeding, less pain and earlier rehabilitation for the patients.

What is claimed is:

1. A two-incision surgical method for minimally invasive total hip arthroplasty, comprising:

positioning a patient in a lateral decubitus position and preoperative preparation;

making a first skin incision over the anterolateral side of the trochanteric area of the femur, intermuscular dissection between the Gluteus medius muscle and Tensor fascia lata muscle, incision of the anterior joint capsule, osteotomy of the femoral neck, removal of the femoral head and neck, acetabular reaming and socket insertion;

making a second skin incision over the Gluteus maximus muscle, dissection through the muscle fiber of the Gluteus maximus, intermuscular dissection between the Gluteus medius and Piriformis muscle incision of the joint capsule, femoral reaming, and femoral stem insertion; and inserting an artificial femoral head, and closing the joint capsule, subcutaneous tissue and skin.

* * * * *